United States Patent
Ertl et al.

(10) Patent No.: US 6,221,633 B1
(45) Date of Patent: Apr. 24, 2001

(54) INSULIN DERIVATIVES HAVING A RAPID ONSET OF ACTION

(75) Inventors: Johann Ertl, Bremthal; Paul Habermann, Eppstein; Karl Geisen, Frankfurt; Gerhard Seipke, Hofheim, all of (DE)

(73) Assignee: Aventis Pharma Deutschland GmbH, Frankfurt am Main (DE)

( * ) Notice: Subject to any disclaimer, the term of this patent is extended or adjusted under 35 U.S.C. 154(b) by 0 days.

(21) Appl. No.: 09/099,307

(22) Filed: Jun. 18, 1998

(30) Foreign Application Priority Data

Jun. 20, 1997 (DE) .............................. 197 26 167

(51) Int. Cl.$^7$ ..................... C12N 15/17; C12N 15/63; C12N 1/21; A61K 38/28; C07K 14/62

(52) U.S. Cl. ..................... 435/69.4; 435/243; 435/320.1; 435/325; 536/23.51; 530/303; 514/3; 514/866

(58) Field of Search ..................... 514/3, 866; 530/303; 435/69.4, 320.1, 325, 243

(56) References Cited

U.S. PATENT DOCUMENTS

| | | |
|---|---|---|
| 3,758,683 | 9/1973 | Jackson . |
| 3,868,358 | 2/1975 | Jackson . |
| 4,614,730 | 9/1986 | Hansen et al. . |
| 4,644,057 | 2/1987 | Bicker et al. . |
| 4,731,405 | 3/1988 | Kirsch et al. . |
| 4,783,441 | 11/1988 | Thurow . |
| 4,885,164 | 12/1989 | Thurow . |
| 5,101,013 | 3/1992 | Dörschug et al. . |
| 5,358,857 | 10/1994 | Stengelin et al. . |
| 5,473,049 | 12/1995 | Obermeier et al. . |
| 5,597,796 | * 1/1997 | Brange . |
| 5,663,291 | 9/1997 | Obermeier et al. . |

FOREIGN PATENT DOCUMENTS

| | | |
|---|---|---|
| 2219 635 | 4/1972 | (DE) . |
| 32 40 177 | 10/1982 | (DE) . |
| 0 018 609 | 4/1980 | (EP) . |
| 0 180 920 | 10/1985 | (EP) . |
| 0 211 299 | 7/1986 | (EP) . |
| 0 214 826 | 8/1986 | (EP) . |
| 0 227 938 | 11/1986 | (EP) . |
| 0 229 956 | 12/1986 | (EP) . |
| 0 305 760 | 8/1988 | (EP) . |
| 0 375 437 | 12/1989 | (EP) . |
| 0 678 522 | 2/1990 | (EP) . |
| 0 600 372 | 11/1993 | (EP) . |
| 0 419 504 | 1/1994 | (EP) . |
| 0 668 292 | 2/1995 | (EP) . |
| WO83/00288 | 2/1983 | (WO) . |
| WO90/07522 | 7/1990 | (WO) . |
| WO92/00321 | 1/1992 | (WO) . |

OTHER PUBLICATIONS

Müller et al., "Insulin Signaling in the Yeast *Saccharomyces cerevisiae* 1. Stimulation of Glucose Metabolism and Snf 1 Kinase by Human Insulin," *Biochemistry*, vol. 37, No. 24, (1998), pp. 8683–8695.
European Search Report for EP Application 98110889.7–2105, Oct. 14, 1998.
Berger, Michael, "Towards more physiological insulin therapy in the 1990s—A comment," *Diabetes Research and Clinical Practice*, 6 (1989), pp. S25–S31.
Bolli, Geremia B., "The pharmacokinetic basis of insulin therapy in diabetes mellitus," *Diabetes Research and Clinical Practice*, 6 (1989), pp. S3–S16.
Dixon, Dr. G.H. et al., "Regeneration of Insulin Activity From the Separated and Inactive A and B Chains," *Nature*, vol. 188, No. 4752 (1960), pp. 721–724.
Drury, P.L. et al., "Diabetic nephropathy," *British Medical Bulletin*, vol. 45, No. 1, (1989), pp 127–147.
Home, P.D. et al., "Insuln treatment: a decade of change," *British Medical Bulletin*, vol. 45, No. 1, (1989), pp. 92–110.
Kang, Steven et al., "Subcutaneous Insulin Absorption Explained by Insulin's Physicochemical Properties—Evidence from Absorption Studies of Soluble Human Insulin and Insulin Analogues in Humans," *Diabetes Care*, vol. 14, No. 11, (1991), pp. 942–948.
Kohner, E.M., "Diabetic retinopathy," *British Medical Bulletin*, vol. 45, No. 1, (1989), pp. 148–173.
Kemmler, Wolfgang et al., "Studies on the Conversion of Proinsulin to Insulin," *The Journal of Biological Chemistry*, vol. 246, No. 22, (1971), pp. 6786–6791.
Nathan. et al., "The Effect of Intensive Treatment of Diabetes on the Development and Progression of Long–Term Complications in Insulin–Dependent Diabetes Mellitus," *The New England Journal of Medicine*, vol. 329, No. 14, (1993), pp. 977–986.
Ward, J.D., "Diabetic neuropathy," *British Medical Bulletin*, vol. 45, No. 1, (1989), pp. 111–126.
German Search Report for Appln. No. 19726167.1, Nov. 24, 1997.

* cited by examiner

Primary Examiner—Christine J. Saoud
(74) Attorney, Agent, or Firm—Finnegan, Henderson, Farabow, Garrett & Dunner, L.L.P.

(57) ABSTRACT

The present invention relates to insulin derivatives which in comparison to human insulin, have an accelerated onset of action, to a process for their preparation and to their use, in particular in pharmaceutical preparations for the treatment of diabetes mellitus. In particular, the present invention relates to insulin derivatives or physiologically tolerable salts thereof in which asparagine (Asn) in position B3 of the B chain is replaced by a naturally occurring basic amino acid residue and at least one amino acid residue in the positions B27, B28 or B29 of the B chain is replaced by another naturally occurring amino acid residue, it optionally being possible for asparagine (Asn) in position 21 of the A chain to be replaced by Asp, Gly, Ser, Thr or Ala and for phenylalanine (Phe) in position B1 of the B chain and the amino acid residue in position B30 of the B chain to be absent.

64 Claims, No Drawings

SEQUENCE LISTING

<160> NUMBER OF SEQ ID NOS: 20

<210> SEQ ID NO 1
<211> LENGTH: 21
<212> TYPE: PRT
<213> ORGANISM: Homo sapiens

<400> SEQUENCE: 1

```
Gly Ile Val Glu Gln Cys Cys Thr Ser Ile Cys Ser Leu Tyr Gln Leu
 1               5                  10                  15

Glu Asn Tyr Cys Asn
            20
```

<210> SEQ ID NO 2
<211> LENGTH: 30

-continued

```
<212> TYPE: PRT
<213> ORGANISM: Homo sapiens

<400> SEQUENCE: 2

Phe Val Asn Gln His Leu Cys Gly Ser His Leu Val Glu Ala Leu Tyr
  1               5                  10                  15

Leu Val Cys Gly Glu Arg Gly Phe Phe Tyr Thr Pro Lys Thr
             20                  25                  30

<210> SEQ ID NO 3
<211> LENGTH: 30
<212> TYPE: PRT
<213> ORGANISM: Homo sapiens

<400> SEQUENCE: 3

Phe Val Lys Gln His Leu Cys Gly Ser His Leu Val Glu Ala Leu Tyr
  1               5                  10                  15

Leu Val Cys Gly Glu Arg Gly Phe Phe Tyr Thr Pro Glu Thr
             20                  25                  30

<210> SEQ ID NO 4
<211> LENGTH: 30
<212> TYPE: PRT
<213> ORGANISM: Homo sapiens

<400> SEQUENCE: 4

Phe Val Lys Gln His Leu Cys Gly Ser His Leu Val Glu Ala Leu Tyr
  1               5                  10                  15

Leu Val Cys Gly Glu Arg Gly Phe Phe Tyr Thr Ile Lys Thr
             20                  25                  30

<210> SEQ ID NO 5
<211> LENGTH: 30
<212> TYPE: PRT
<213> ORGANISM: Homo sapiens

<400> SEQUENCE: 5

Phe Val Lys Gln His Leu Cys Gly Ser His Leu Val Glu Ala Leu Tyr
  1               5                  10                  15

Leu Val Cys Gly Glu Arg Gly Phe Phe Tyr Ile Pro Lys Thr
             20                  25                  30

<210> SEQ ID NO 6
<211> LENGTH: 97
<212> TYPE: PRT
<213> ORGANISM: Homo sapiens

<400> SEQUENCE: 6

Met Ala Thr Thr Ser Thr Gly Asn Ser Ala Arg Phe Val Lys Gln His
  1               5                  10                  15

Leu Cys Gly Ser His Leu Val Glu Ala Leu Tyr Leu Val Cys Gly Glu
             20                  25                  30

Arg Gly Phe Phe Tyr Thr Pro Glu Thr Arg Arg Glu Ala Glu Asp Pro
         35                  40                  45

Gln Val Gly Gln Val Glu Leu Gly Gly Pro Gly Ala Gly Ser Leu
     50                  55                  60

Gln Pro Leu Ala Leu Glu Gly Ser Leu Gln Lys Arg Gly Ile Val Glu
 65                  70                  75                  80

Gln Cys Cys Thr Ser Ile Cys Ser Leu Tyr Gln Leu Glu Asn Tyr Cys
                 85                  90                  95
```

Asn

<210> SEQ ID NO 7
<211> LENGTH: 97
<212> TYPE: PRT
<213> ORGANISM: Homo sapiens

<400> SEQUENCE: 7

Met Ala Thr Thr Ser Thr Gly Asn Ser Ala Arg Phe Val Lys Gln His
1               5                   10                  15

Leu Cys Gly Ser His Leu Val Glu Ala Leu Tyr Leu Val Cys Gly Glu
            20                  25                  30

Arg Gly Phe Phe Tyr Thr Ile Lys Thr Arg Arg Glu Ala Glu Asp Pro
        35                  40                  45

Gln Val Gly Gln Val Glu Leu Gly Gly Gly Pro Gly Ala Gly Ser Leu
    50                  55                  60

Gln Pro Leu Ala Leu Glu Gly Ser Leu Gln Lys Arg Gly Ile Val Glu
65                  70                  75                  80

Gln Cys Cys Thr Ser Ile Cys Ser Leu Tyr Gln Leu Glu Asn Tyr Cys
                85                  90                  95

Asn

<210> SEQ ID NO 8
<211> LENGTH: 97
<212> TYPE: PRT
<213> ORGANISM: Homo sapiens

<400> SEQUENCE: 8

Met Ala Thr Thr Ser Thr Gly Asn Ser Ala Arg Phe Val Lys Gln His
1               5                   10                  15

Leu Cys Gly Ser His Leu Val Glu Ala Leu Tyr Leu Val Cys Gly Glu
            20                  25                  30

Arg Gly Phe Phe Tyr Ile Pro Lys Thr Arg Arg Glu Ala Glu Asp Pro
        35                  40                  45

Gln Val Gly Gln Val Glu Leu Gly Gly Gly Pro Gly Ala Gly Ser Leu
    50                  55                  60

Gln Pro Leu Ala Leu Glu Gly Ser Leu Gln Lys Arg Gly Ile Val Glu
65                  70                  75                  80

Gln Cys Cys Thr Ser Ile Cys Ser Leu Tyr Gln Leu Glu Asn Tyr Cys
                85                  90                  95

Asn

<210> SEQ ID NO 9
<211> LENGTH: 21
<212> TYPE: PRT
<213> ORGANISM: Homo sapiens

<400> SEQUENCE: 9

Gly Ile Val Glu Gln Cys Cys Thr Ser Ile Cys Ser Leu Tyr Gln Leu
1               5                   10                  15

Glu Asn Tyr Cys Asp
            20

<210> SEQ ID NO 10
<211> LENGTH: 30
<212> TYPE: PRT
<213> ORGANISM: Homo sapiens

<400> SEQUENCE: 10

Phe Val Lys Gln His Leu Cys Gly Ser His Leu Val Glu Ala Leu Tyr
 1               5                  10                  15

Leu Val Cys Gly Glu Arg Gly Phe Phe Tyr Thr Ile Lys Thr
            20                  25                  30

<210> SEQ ID NO 11
<211> LENGTH: 97
<212> TYPE: PRT
<213> ORGANISM: Homo sapiens

<400> SEQUENCE: 11

Met Ala Thr Thr Ser Thr Gly Asn Ser Ala Arg Phe Val Lys Gln His
 1               5                  10                  15

Leu Cys Gly Ser His Leu Val Glu Ala Leu Tyr Leu Val Cys Gly Glu
                20                  25                  30

Arg Gly Phe Phe Tyr Thr Ile Lys Thr Arg Arg Glu Ala Glu Asp Pro
            35                  40                  45

Gln Val Gly Gln Val Glu Leu Gly Gly Pro Gly Ala Gly Ser Leu
    50                  55                  60

Gln Pro Leu Ala Leu Glu Gly Ser Leu Gln Lys Arg Gly Ile Val Glu
65                  70                  75                  80

Gln Cys Cys Thr Ser Ile Cys Ser Leu Tyr Gln Leu Glu Asn Tyr Cys
                85                  90                  95

Asp

<210> SEQ ID NO 12
<211> LENGTH: 18
<212> TYPE: DNA
<213> ORGANISM: Homo sapiens

<400> SEQUENCE: 12
tttgtgaagc agcacctg                                                       18

<210> SEQ ID NO 13
<211> LENGTH: 18
<212> TYPE: DNA
<213> ORGANISM: Homo sapiens

<400> SEQUENCE: 13
caggtgctgc ttcacaaa                                                       18

<210> SEQ ID NO 14
<211> LENGTH: 28
<212> TYPE: DNA
<213> ORGANISM: Homo sapiens

<400> SEQUENCE: 14
ttctacacac ccgagacccg cggcatcg                                            28

<210> SEQ ID NO 15
<211> LENGTH: 29
<212> TYPE: DNA
<213> ORGANISM: Homo sapiens

<400> SEQUENCE: 15
gccgcgggtc tcgggtgtgt agaagaagc                                           29

<210> SEQ ID NO 16
<211> LENGTH: 23
<212> TYPE: DNA

-continued

```
<213> ORGANISM: Homo sapiens

<400> SEQUENCE: 16
ttctacatcc ccaagacccg ccg                                           23

<210> SEQ ID NO 17
<211> LENGTH: 24
<212> TYPE: DNA
<213> ORGANISM: Homo sapiens

<400> SEQUENCE: 17
cttggggatg tagaagaagc ctcg                                          24

<210> SEQ ID NO 18
<211> LENGTH: 24
<212> TYPE: DNA
<213> ORGANISM: Homo sapiens

<400> SEQUENCE: 18
tacacaatca agacccgccg ggag                                          24

<210> SEQ ID NO 19
<211> LENGTH: 27
<212> TYPE: DNA
<213> ORGANISM: Homo sapiens

<400> SEQUENCE: 19
ggtcttgatt gtgtagaaga agcctcg                                       27

<210> SEQ ID NO 20
<211> LENGTH: 39
<212> TYPE: DNA
<213> ORGANISM: Homo sapiens

<400> SEQUENCE: 20 tttttttgtcg actattagtc gcagtagttc taccagctg                         39
```

INSULIN DERIVATIVES HAVING A RAPID ONSET OF ACTION

The present invention relates to insulin derivatives which, in comparison to human insulin, have an accelerated onset of action, to a process for their preparation and to their use, in particular in pharmaceutical preparations for the treatment of diabetes mellitus.

Approximately 120 million people worldwide suffer from diabetes mellitus. Among these are approximately 12 million type I diabetics, for whom the administration of insulin is the only therapy possible at present. The affected people are assigned insulin injections, as a rule several times daily, for life. Although type II diabetes, from which approximately 100 million people suffer, is not fundamentally accompanied by an insulin deficiency, in a large number of cases, however, treatment with insulin is regarded as the most favorable or only possible form of therapy.

With increasing length of the disease, a large number of the patients suffer from so-called diabetic late complications. These are essentially micro- and macrovascular damage, which depending on the type and extent, result in kidney failure, blindness, loss of extremities or an increased risk of heart/circulation disorders.

As a cause, chronically increased blood glucose levels are primarily held responsible, since even with careful adjustment of the insulin therapy a normal blood glucose profile, such as would correspond to physiological regulation, is not achieved (Ward, J. D. (1989) British Medical Bulletin 45, 111–126; Drury, P. L. et al. (1989) British Medical Bulletin 45, 127–147; Kohner, E. M. (1989) British Medical Bulletin 45, 148–173)

In healthy people, insulin secretion is closely dependent on the glucose concentration of the blood. Increased glucose levels, such as occur after meals, are rapidly compensated by an increased release of insulin. In the fasting state, the plasma insulin level falls to a basal value, which is sufficient to guarantee a continuous supply of insulin-sensitive organs and tissue with glucose. An optimization of the therapy, the so-called intensified insulin therapy, is today primarily aimed at keeping variations in the blood glucose concentration, especially deviations upward, as low as possible (Bolli, G. B. (1989) Diabetes Res. Clin. Pract. 6, p. 3–p. 16; Berger, M. (1989) Diabetes Res. Clin. Pract. 6, p. 25–p. 32). This leads to a significant decrease in the occurrence and the progression of diabetic late damage (The Diabetes Control and Complications Trial Research Group (1993) N. Engl. J. Med. 329, 977–986).

From the physiology of insulin secretion, it can be deduced that for an improved, intensified insulin therapy using subcutaneously administered preparations, two insulin preparations having different pharmacodynamics are needed. To compensate the blood glucose rise after meals, the insulin must flow in rapidly and must only act for a few hours. For the basal supply, in particular in the night, a preparation should be available which acts for a long time, has no pronounced maximum and only infuses very slowly.

The preparations based on human and animal insulins only fulfill the demands of an intensified insulin therapy, however, in a restricted manner. After subcutaneous administration, rapidly acting insulins (unmodified insulins) pass too slowly into the blood and to the site of action and have too long an overall duration of action. The result is that the postprandial glucose levels are too high and the blood glucose begins to fall severely several hours after the meal (Kang, S. et al. (1991) Diabetes Care 14, 142–148; Home, P. J. et al. (1989) British Medical Bulletin 45, 92–110; Bolli, G. B. (1989) Diabetes Res. Clin. Pract. 6, p. 3–p. 16). The available basal insulins in turn, especially NPH insulins, have too short a duration of action and have a too severely pronounced maximum.

Beside the possibility of affecting the profile of action by means of pharmaceutical principles, the alternative presents itself today of designing insulin derivatives, with the aid of genetic engineering, which achieve specific properties such as onset and duration of action solely by means of their structural properties. By the use of suitable insulin derivatives, a significantly better adjustment of the blood glucose more closely adapted to the natural conditions could therefore be achieved.

Insulin derivatives having an accelerated onset of action are described in EP 0 214 826, EP 0 375 437 and EP 0 678 522. EP 0 214 826 relates, inter alia, to substitutions of B27 and B28, but not in combination with the substitution of B3. EP 0 678 522 describes insulin derivatives which have various amino acids, preferably proline, but not glutamic acid, in the position B29. EP 0 375 437 encompasses insulin derivatives having lysine or arginine in B28, which can optionally be additionally modified in B3 and/or A21.

EP 0 419 504 discloses insulin derivatives which are protected against chemical modifications by changing asparagine in B3 and at least one further amino acid in the positions A5, A15, A18 or A21. Combinations with modifications in positions B27, B28 or B29 are, however, not described. An indication that these compounds have modified pharmacodynamics resulting in a more rapid onset of action is not given.

WO 92/00321 describes insulin derivatives in which at least one amino acid of the positions B1–B6 is replaced by lysine or arginine. According to WO 92/00321, insulins of this type have a prolonged action. Combinations with modifications of the positions B27, 28, 29, however, are not disclosed.

BRIEF DESCRIPTION OF THE DRAWING

The FIGURE shows the pharmacodynamics of insulin and derivatives according to the invention after subcutaneous administration to dogs. The mean glucose infusion rate from the time of injection (T=0) through 240 minutes is shown for insulin and selected derivatives according to the invention.

The object of the present invention is to prepare insulin derivatives which after administration, in particular after subcutaneous administration, have an onset of action which is accelerated in comparison with human insulin.

Insulin derivatives are derivatives of naturally occurring insulins, namely human insulin (see SEQ ID NO 1=A chain of human insulin; see SEQ ID NO 2=B chain of human insulin, sequence listing) or animal insulins which differ from the corresponding, otherwise identical naturally occurring insulin by substitution of at least one naturally occurring amino acid residue and/or addition of at least one amino acid residue and/or organic residue.

It is further an object of the present invention to provide a process for the preparation of the insulin derivatives having the property mentioned, the corresponding intermediates and their precursors.

The object is achieved by an insulin derivative or a physiologically tolerable salt thereof in which asparagine (Asn) in position B3 of the B chain is replaced by a naturally occurring basic amino acid residue and at least one amino acid residue in the positions B27, B28 or B29 of the B chain is replaced by another naturally occurring amino acid residue, it optionally being possible for asparagine (Asn) in position 21 of the A chain to be replaced by Asp, Gly, Ser, Thr or Ala and for phenylalanine (Phe) in position B1 of the B chain and the amino acid residue in position B30 of the B chain to be absent.

Preferably, the insulin derivative or its physiologically tolerable salt is of formula I

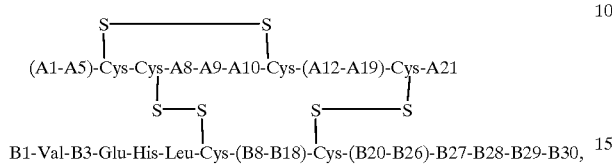

in which
(A1–A5) are the amino acid residues in the positions A1 to A5 of the A chain of human insulin (cf. SEQ ID NO 1) or animal insulin,
(A12–A19) are the amino acid residues in the positions A12 to A19 of the A chain of human insulin (cf. SEQ ID NO 1) or animal insulin,
(B8–B18) are the amino acid residues in the positions B8 to B18 of the B chain of human insulin (cf. SEQ ID NO 2) or animal insulin,
(B20–B26) are the amino acid residues in the positions B20 to B26 of the B chain of human insulin (cf. SEQ ID NO 2) or animal insulin,
A8, A9, A10 are the amino acid residues in the positions A8, A9 and A10 of the A chain of human insulin (cf. SEQ ID NO 1) or animal insulin,
A21 is Asn, Asp, Gly, Ser, Thr or Ala,
B30 is —OH or the amino acid residue in position B30 of the B chain of human insulin (cf. SEQ ID NO 2) or animal insulin,
B1 is a phenylalanine residue (Phe) or a hydrogen atom,
B3 is a naturally occurring basic amino acid residue,
B27, B28 and B29 are the amino acid residues in the positions B27, B28 and B29 of the B chain of human insulin (cf. SEQ ID NO 2) or animal insulin or in each case are another naturally occurring amino acid residue, where at least one of the amino acid residues in the positions B27, B28 and B29 of the B chain is replaced by another naturally occurring amino acid residue.

Of the twenty naturally occurring amino acids which are genetically encodable, the amino acids glycine (Gly), alanine (Ala), valine (Val), leucine (Leu), isoleucine (Ile), serine (Ser), threonine (Thr), cysteine (Cys), methionine (Met), asparagine (Asn), glutamine (Gln), phenylalanine (Phe), tyrosine (Tyr), tryptophan (Trp) and proline (Pro) are designated here as neutral amino acids, the amino acids arginine (Arg), lysine (Lys) and histidine (His) are designated as basic amino acids and the amino acids aspartic acid (Asp) and glutamic acid (Glu) are designated as acidic amino acids.

Preferably, the insulin derivative or its physiologically tolerable salt according to the present invention is a derivative of bovine insulin, porcine insulin or human insulin, namely an insulin derivative or a physiologically tolerable salt thereof of the formula 1, which is distinguished in that
A8 is alanine (Ala),
A9 is serine (Ser),
A10 is valine (Val) and
B30 is alanine (Ala) (amino acid residues A8 to A10 and B30 of bovine insulin), A8 is threonine (Thr),
A9 is serine (Ser) and
A10 is isoleucine (Ile) (amino acid residues A8 to A10 of the insulins of man or pigs), where
B30 is alanine (Ala) (amino acid residue B30 of porcine insulin) or
B30 is threonine (Thr) (amino acid residue B30 of human insulin, cf. SEQ ID NO 2).

Particularly preferably, an insulin derivative or a physiologically tolerable salt thereof of the formula I with the amino acid residues A8 to A10 and B30 of human insulin is one which is furthermore distinguished in that
(A1–A5) are the amino acid residues in the positions A1 to A5 of the A chain of human insulin (cf. SEQ ID NO 1),
(A12–A19) are the amino acid residues in the positions A12 to A19 of the A chain of human insulin (cf. SEQ ID NO 1),
(B8–B18) are the amino acid residues in the positions B8 to B18 of the B chain of human insulin (cf. SEQ ID NO 2) and
(B20–B26) are the amino acid residues in the positions B20 to B26 of the B chain of human insulin (cf. SEQ ID NO 2).

Further preferred embodiments of the present invention are an insulin derivative or a physiologically tolerable salt thereof of the formula 1, wherein the amino acid residue in position B1 of the B chain is a phenylalanine residue (Phe) or
an insulin derivative or a physiologically tolerable salt thereof of the formula 1, wherein the amino acid residue in position B3 of the B chain is a histidine (His), lysine (Lys) or arginine residue (Arg).

Further preferred embodiments of the present invention are an insulin derivative or a physiologically tolerable salt thereof of the formula 1, wherein at least one of the amino acid residues in the positions B27, B28 and B29 of the B chain is replaced by a naturally occurring amino acid residue which is selected from the group consisting of the neutral or of the acidic amino acids,
an insulin derivative or a physiologically tolerable salt thereof of the formula I, wherein at least one of the amino acid residues in the positions B27, B28 and B29 of the B chain is a naturally occurring amino acid residue which is selected from the group consisting of isoleucine (Ile), aspartic acid (Asp) and glutamic acid (Glu), preferably wherein at least one of the amino acid residues in the positions B27, B28 of the B chain is replaced by a naturally occuring amino acid residue which is selected from the group consisting of the neutral amino acids, or particularly preferably wherein at least one of the amino acid residues in the positions B27, B28 and B29 of the B chain is an isoleucine residue (Ile), or
an insulin derivative or a physiologically tolerable salt thereof of the formula I, wherein at least one of the amino acid residues in the positions B27, B28 and B29 of the B chain is a naturally occurring amino acid residue which is selected from the group consisting of the acidic amino acids, preferably wherein at least one of the amino acid residues in the positions B27, B28 and B29 of the B chain is an aspartic acid residue (Asp), preferably wherein the amino acid residue in position B27 or B28 of the B chain is an aspartic acid residue (Asp), or wherein at least one of the amino acid residues in the positions B27, B28 and B29 of the B chain is a glutamic acid residue (Glu).

A preferred embodiment of the present invention is also an insulin derivative or a physiologically tolerable salt thereof of the formula I, wherein the amino acid residue in position B29 of the B chain is an aspartic acid residue (Asp).

Further preferred embodiments are an insulin derivative or a physiologically tolerable salt thereof of the formula I, wherein the amino acid residue in position B27 of the B chain is a glutamic acid residue (Glu), an insulin derivative or a physiologically tolerable salt thereof of the formula I, wherein the amino acid residue in position B28 of the B chain is a glutamic acid residue (Glu), or an insulin derivative or a physiologically tolerable salt thereof of the formula I, wherein the amino acid residue in position B29 of the B chain is a glutamic acid residue (Glu).

Very particularly preferably, an insulin derivative or a physiologically tolerable salt thereof is one which is distinguished in that the B chain has the sequence
Phe Val Lys Gln His Leu Cys Gly Ser His Leu Val Glu Ala Leu Tyr Leu Val Cys Gly Glu Arg Gly Phe Phe Tyr Thr Pro Glu Thr
(SEQ ID NO 3), for example Lys (B3), Glu (B29)-human insulin, or an insulin derivative or a physiologically tolerable salt thereof which is distinguished in that the amino acid residue in position B27 of the B chain is an isoleucine residue (Ile), preferably an insulin derivative or a physiologically tolerable salt thereof which is distinguished in that the B chain has the sequence
Phe Val Lys Gln His Leu Cys Gly Ser His Leu Val Glu Ala Leu Tyr Leu Val Cys Gly Glu Arg Gly Phe Phe Tyr Ile Pro Lys Thr
(SEQ ID NO 5), for example Lys (B3), Ile (B27)-human insulin, or an insulin derivative or a physiologically tolerable salt thereof of the formula I, wherein the amino acid residue in position B28 of the B chain is an isoleucine residue (Ile), preferably an insulin derivative or a physiologically tolerable salt thereof which is distinguished in that the B chain has the sequence
Phe Val Lys Gln His Leu Cys Gly Ser His Leu Val Glu Ala Leu Tyr Leu Val Cys Gly Glu Arg Gly Phe Phe Tyr Thr Ile Lys Thr
(SEQ ID NO 4), for example Lys (B3), Ile (B28)-human insulin.

Particularly preferably, an insulin derivative or a physiologically tolerable salt thereof of the formula I, which is distinguished in that the amino acid residue in position B28 of the B chain is an isoleucine residue (Ile) and the amino acid residue in position A21 is an asparagine residue (Asp), is preferably one wherein the A chain has the sequence
Gly Ile Val Glu Gln Cys Cys Thr Ser Ile Cys Ser Leu Tyr Gln Leu Tyr Gln Leu Glu Asn Tyr Cys Asp (SEQ ID NO.: 9) and the B chain has the sequence
Phe Val Lys Gln His Leu Cys Gly Ser His Leu Val Glu Ala Leu Tyr Leu Val Cys Gly Glu Arg Gly Phe Phe Pyr Thr Ile Lys Thr (SEQ ID NO.: 10)
(Lys (B3), Ile (B28), Asp (A21)-human insulin).

The insulin derivatives of the formula I can preferably be prepared by genetic engineering.

The object set at the outset is accordingly further achieved by a process for the preparation of an insulin derivative or of a physiologically tolerable salt thereof of the formula I, comprising the construction of a replicable expression vehicle which contains a DNA sequence which codes for a precursor of the insulin derivative in which the amino acid residue in position A1 of the A chain is linked to the amino acid residue B30 of the B chain via a peptide chain of the formula II $$—R^1_n—Arg— \qquad\qquad II$$

in which $R^1_n$ is a peptide chain having n amino acid residues and n is an integer from 0 to 34, and the B chain is prolonged in position B1 by a peptide chain of the formula III $$Met-R^2_m—(Arg)_p— \qquad\qquad III$$

in which $R^2_m$ is a peptide chain having m amino acid residues, m is an integer from 0 to 40, preferably from 0 to 9, and p is 0, 1 or 2, where for p=0 the peptide chain $R^2_m$ preferably ends with Lys, expression in a host cell and release of the insulin derivative from its precursor using chemical and/or enzymatic methods.

Preferably, the process is one wherein the host cell is a bacterium, particularly preferably one wherein the bacterium is *E. coli*.

Preferably, the process is one wherein the host cell is a yeast, particularly preferably one wherein the yeast is *Saccharomyces cerevisiae*.

For the preparation of an insulin derivative having the amino acid sequences SEQ ID NO.: 9 (A chain) and SEQ ID NO.: 10 (B chain), the precursor of this insulin derivative preferably has the sequence
Met Ala Thr Thr Ser Thr Gly Asn Ser Ala Arg Phe Val Lys Gln His Leu Cys Gly Ser His Leu Val Glu Ala Leu Tyr Leu Val Cys Gly Glu Arg Gly Phe Phe Tyr Thr Ile Lys Thr Arg Arg Glu Ala Glu Asp Pro Gln Val Gly Gln Val Glu Leu Gly Gly Gly Pro Gly Ala Gly Ser Leu Gln Pro Leu Ala Leu Glu Gly Ser Leu Gln Lys Arg Gly Ile Val Glu Gln Cys Cys Thr Ser Ile Cys Ser Leu Tyr Gln Ley Glu Asn Tyr Cys Asp (SEQ ID NO.: 11),
a Lys (B3), Ile (B28), Asp (A21)-preproinsuLin.

For the preparation of an insulin derivative having the amino acid sequence SEQ ID NO 3, the precursor of this insulin derivative preferably has the sequence
Met Ala Thr Thr Ser Thr Gly Asn Ser Ala Arg Phe Va Lys Gln His Leu Cys Gly Ser His Leu Val Glu Ala Leu Tyr Leu Val Cys Gly Glu Arg Gly Phe Phe Tyr Thr Pro Glu Thr Arg Arg Glu Ala Glu Asp Pro Gln Val Gly Gln Val Glu Leu Gly Gly Gly Pro Gly Ala Gly Ser Leu Gln Pro Leu Ala Leu Glu Gly Ser Leu Gln Lys Arg Gly Ile Val Glu Gln Cys Cys Thr Ser Ile Cys Ser Leu Tyr Gln Leu Glu Asn Tyr Cys Asn (Lys (B3), Glu (829)-preproinsulin)
(SEQ ID NO 6).

For the preparation of an insulin derivative having the amino acid sequence SEQ ID NO 5, the precursor of this insulin derivative preferably has the sequence
Met Ala Thr Thr Ser Thr Gly Asn Ser Ala Arg Phe Val Lys Gln His Leu Cys Gly Ser His Leu Val Glu Ala Leu Tyr Leu Val Cys Gly Glu Arg Gly Phe Phe Tyr Ile Pro Lys Thr Arg Arg Glu Ala Glu Asp Pro Gln Val Gly Gln Val Gu Leu Gly Gly Gly Pro Gly Ala Gly Ser Leu Gln Pro Leu Ala Leu Glu Gly Ser Leu Gln Lys Arg Gly Ile Val Glu Gln Cys Cys Thr Ser Ile Cys Ser Leu Tyr Gln Leu Glu Asn Tyr Cys Asn (Lys (B3), Ile (B27)-preproinsulin)
(SEQ ID NO 8).

For the preparation of an insulin derivative having the amino acid sequence SEQ ID NO 4, the precursor of this insulin derivative preferably has the sequence
Met Ala Thr Thr Ser Thr Gly Asn Ser Ala Arg Phe Val Lys Gln His Leu Cys Gly Ser His Leu Val Glu Ala Leu Tyr Leu Val Cys Gly Glu Arg Gly Phe Phe Tyr Thr Ile Lys Thr Arg Arg Glu Ala Glu Asp Pro Gln Val Gly Gln Val Glu Leu Gly Gly Gly Pro Gly Ala Gly Ser Leu Gln Pro Leu Ala Leu Glu Gly Ser Leu Gln Lys Arg Gly Ile Val Glu Gln Cys Cys Thr Ser Ile Cys Ser Leu Tyr Gln Leu Glu Asn Tyr Cys Asn (Lys (B3), Ile (B28)-preproinsulin)
(SEQ ID NO 7).

The present invention accordingly also relates to said precursors of the preferred insulin derivatives, namely the peptides having the sequence numbers SEQ ID NO.: 11, SEQ ID NO 6, SEQ ID NO 7 and SEQ ID NO 8, the DNA sequences which code for said precursors, the expression vehicles which comprise these DNA sequences and the host cells which are transformed using these expression vehicles.

The insulin derivatives of the formula I are mainly prepared by genetic engineering by means of site-directed mutagenesis according to standard methods.

To do this, a gene structure coding for the desired insulin derivative of the formula I is constructed and expressed in a host cell—preferably in a bacterium such as *E. coli* or a yeast, in particular *Saccharomyces cerevisiae*—and—if the gene structure codes for a fusion protein—the insulin derivative of the formula I is released from the fusion protein; analogous methods are described, for example, in EP-A-0 211 299, EP-A-0 227 938, EP-A-0 229 998, EP-A-0 286 956 and the DE patent application P 38 21 159.

The removal of the fusion protein component can be carried out chemically by cell disruption by means of cyanogen halide (see EP-A-0 180 920).

In the preparation by means of a preproinsulin precursor which has a fusion protein component (presequence) according to U.S. Pat. No. 5,358,857, the removal of the fusion protein component takes place in a later stage together with the removal of the C peptide.

The insulin precursor is then subjected to oxidative sulfitolysis according to the method described, for example, by R. C. Marshall and A. S. Inglis in "Practical Protein Chemistry—A Handbook" (Publisher A. Darbre) 1986, pages 49–53 and then renatured in the presence of a thiol with formation of the correct disulfide bridges, e.g. according to the method described by G. H. Dixon and A. C. Wardlow in Nature (1960), pages 721–724. The insulin precursors, however, can also be folded directly (EP-A-0 600 372; EP-A-0 668 292).

The C peptide is removed by means of tryptic cleavage—e.g. according to the method of Kemmler et al., J. B. C. (1971), pages 6786–6791 and the insulin derivative of the formula I is purified by means of known techniques such as chromatography—e.g. EP-A-0 305 760—and crystallization.

If n in formula II is 0, tryptic cleavage serves to sever the peptide bond between A and B chains.

In this process, the B chain C terminal ends with arginine or two arginine residues. These can be removed enzymatically by means of carboxy-peptidase B.

The insulin derivatives according to the invention have full biological activity. This was shown by intravenous administration to rabbits and the blood glucose fall resulting therefrom (Examples 5 and 6).

The more rapid onset of action after subcutaneous administration was shown in fasting dogs using the euglycemic clamp technique (Example 7). 0.3 IU/kg was administered. The reference preparation was human insulin. In the clamp technique, the blood glucose value is measured at short time intervals after insulin injection and exactly the amount of glucose to compensate the fall is infused. This has the advantage that no counter-regulation occurs with the animals, as would be the case with a severe fall in the blood glucose after the administration of insulin. The amount and the time course of the infused glucose characterize the action of the insulin. Lys(B3), Glu(B29)—(SEQ ID NO 3) and Lys(B3), Ile(B28)—(SEQ ID NO 4) insulin have a clearly more rapid onset of action than human insulin. The maximum action (glucose infusion rate) is achieved after 100 minutes with human insulin, after 80 minutes, however, with Lys(B3), Glu(B29)-insulin (SEQ ID NO 3) and already after 60 minutes with Lys(B3)—, Ile(B28)-insulin (SEQ ID NO 4). Therefore these analogs, when they are injected shortly before a meal, should compensate the postprandial rise in the blood glucose better than human insulin.

The insulin derivatives described are therefore suitable both for the therapy of type I and of type II diabetes mellitus, preferably in combination with a basal insulin.

The present invention therefore also relates to the use of the insulin derivative and/or its physiologically tolerable salt of the formula I for the production of a pharmaceutical preparation which has an insulin activity with a rapid onset of action.

A suitable carrier medium which is physiologically acceptable and compatible with the insulin derivative is a sterile aqueous solution which is made isotonic with blood in the customary manner, e.g. by means of glycerol, sodium chloride, glucose, and in addition contains one of the customary preservatives, e.g. phenol, m-cresol or p-hydroxybenzoic acid ester. The carrier medium can additionally contain a buffer substance, e.g. sodium acetate, sodium citrate, sodium phosphate. For adjustment of the pH, dilute acids (typically HCl) or alkalis (typically NaOH) are used. The preparation can furthermore contain zinc ions.

The insulin derivatives can be employed in the pharmaceutical preparations even in the form of their physiologically tolerable salts, as alkali metal or as ammonium salts. Any desired proportion of one or more insulin derivatives of the formula I or an insulin derivative of the formula I can be present in a mixture of other of these insulin derivatives independently of one another in each case in dissolved, amorphous and/or crystalline form.

It is sometimes advantageous to add to the preparation according to the invention a suitable amount of a suitable stabilizer which prevents the precipitation of protein under thermomechanical stress on contact with various materials. Such stabilizers are disclosed, for example, in EP-A-18609, DE-A 32 40 177 or in WO-83/00288.

The present invention further relates to a pharmaceutical preparation which comprises at least one insulin derivative and/or a physiologically tolerable salt thereof of the formula I, preferably in dissolved, amorphous and/or crystalline form.

The insulin derivatives according to the invention have a rapid onset of action. In practical insulin therapy, it is customary under certain circumstances to mix rapid-acting insulins with preparations which contain a depot auxiliary (e.g. NPH insulin). Depending on the composition, preparations result from this whose profiles of action correspond to the superimposed individual profiles provided the individual components in the mixture are stable and are not mutually affected. When mixing an insulin derivative with human NPH insulin, however, it is to be expected that, particularly on long-term storage, an exchange takes place between the dissolved derivative and the crystalline NPH insulin. As a result of this both the pharmacodynamics of the depot insulin and those of the dissolved rapidly acting insulin are changed in an unforeseeable manner. In order to avoid this, it is sensible to prepare the rapidly acting derivative using a depot auxiliary—for example as NPH insulin. This depot form of the insulin derivative can then be mixed as desired with the dissolved rapidly acting form without the composition of one or the other form changing in the course of storage due to exchange.

Although the invention in essence relates to rapidly acting insulin derivatives, it accordingly, however, also comprises the possibility of preparing derivatives of this type as a depot form for the purpose of miscibility, the depot auxiliary preferably being protamine sulfate and the insulin derivative and/or its physiologically tolerable salt being present with the protamine sulfate in a cocrystallizate.

The present invention further relates to an injectable solution which comprises the pharmaceutical preparations described above in dissolved form.

EXAMPLES

Example 1

Construction of Lys (B3)-proinsulin as a Starting Point for the Plasmids Relevant to the Invention Corresponding to Examples 2–4

U.S. Pat. No. 5,358,857 describes the vector pINT 90d and the PCR primers Tir and Insu 11. These components serve as starting materials for the construction of a plasmid pINT 125d, which codes for the desired Lys (B3)-proinsulin.

Additionally, the primers Insu 35 having the sequence

5' TTT GTG AAG CAG CAC CTG 3' (SEQ ID NO: 12)

and Insu 36 having the sequence

5' CAG GTG CTG CTT CAC AAA 3' (SEQ ID NO: 12)

are synthesized.

A PCR reaction is carried out using the primers Tir and Insu 36 and a second reaction is carried out using the primers Insu 11 and Insu 35. The template used for this is pINT 90d DNA.

The products of the two PCR reactions are partially complementary, such that when they are combined in a third PCR reaction with the primers Tir and Insu 11 they afford a fragment which codes for a proinsulin variant which contains the B chain lysine in position 3. This PCR fragment is precipitated in ethanol for purification, dried and then digested with the restriction enzymes Nco 1 and Sal 1 according to the instructions of the manufacturer. The reaction mixture is separated by gel electrophoresis and the desired Nco 1/Sal 1 fragment is isolated.

The application cited describes a plasmid pINT 91d which codes for a mini-proinsulin. If the sequence coding for mini-proinsulin is excised by means of Nco 1 and Sal 1 and the residual plasmid DNA is isolated, this residual plasmid DNA can be reacted with the shown Nco 1/Sal 1 PCR fragment in a T 4 ligase reaction to give the plasmid pINT 125d. This is transformed by E. coli K12, replicated therein and reisolated. After verification of the plasmid structure by means of DNA sequence and restriction analysis, pINT 125d DNA is used as template DNA for the introduction of further mutations into this proinsulin variant.

Example 2

Construction of Lys (B3) Glu (B29)-proinsulin

For the preparation of the mutein, the primers 329a having the sequence

5' TTC TAC ACA CCC GAG ACC CGC GGC ATC G-3' (SEQ ID NO: 13)

and 329b having the sequence

5' GCC GCG GGT CTC GGG TGT GTA GAA GAA GC 3' (SEQ ID NO: 14)

are synthesized.

The template used is DNA of the plasmids pINT125d and pINT91d. Primer 329a is reacted with the primer Insu 11 on the template pINT91d and primer 329b is reacted with Tir (see above example) on the template pINT125d in a PCR reaction. Since both PCR products are partially complementary, they can be combined in a direct PCR reaction and reacted again with the primers Tir and Insu 11. A DNA fragment results which codes for the desired mutein. This fragment is double-digested using the restriction enzymes Nco 1 and Sal 1 and the resulting Nco 1/Sal 1 fragment is inserted into the pINT 91 d residual plasmid DNA in a T4 ligase reaction.

The plasmid pINT 329 results, which after amplification in E. coli K12 by means of restriction and DNA sequence analysis is verified with respect to the desired structure.

The proinsulin derivative encoded by the plasmid is characterized by the two amino acid replacements and a C-bonding member which consists of the amino acid arginine.

Example 3

Construction of Lys (B3) Ile (B27)-proinsulin

The construction is carried out according to the preceding example using the primer pairs

KB3 JB 27A

5' TTC TAC ATC CCC AAG ACC CGC CG 3' (SEQ ID NO: 15)

and Insu 11 and also

K B3 J 27B

5' CTT GGG GAT GTA GAA GAA GCC TCG 3' (SEQ ID NO: 16)

and Tir.

The template used in both PCR reactions is DNA of the plasmid pINT125d. The PCR products of both reactions are combined in a third reaction, as described in Example 1, and the product is cloned corresponding to the example.

The plasmid pINT332 results.

Example 4

Construction of Lys (B3) Ile (B28)-proinsulin

The construction is carried out according to Example 3 using the primer pairs:

KB3 JB 28A

5' TAC ACA ATC AAG ACC CGC CGG GAG-3' (SEQ ID NO: 17)

and Insu 11 and also

KB J B28B

5' GGT CTT GAT TGT GTA GM GM GCC TCG-3' (SEQ ID NO: 18)

and Tir.

The plasmid pINT 333 results.

Expression of the constructed insulin variants

The plasmids pINT 329, 332 and 333 are each transformed by way of example by E. coli K12 W3110. Recombinant bacteria which contain plasmids which encode the respective variants are then fermented according to Example 4 of the US patent having the U.S. Pat. No. 5,227,293 and the desired raw material for the production of the respective insulin variants is thus produced.

Example 5

Construction of Lys (B3), Ile (B28), Asp (A21)-proinsulin

Construction is carried out as in Example 3. instead of pINT125d, however, the template serving for the PCR reaction is DNA of the plasmid pINT333, which was constructed in Example 4. The following primer pair is used here:

P-pint 365

5'-TTTTTGTCGACTATTAGTCGCAGTAGTTCTAC CAGCTG-3' (SEQ ID NO: 19)

and Tir.

The plasmid pINT365 results.

Example 6

Biological Activity of Lys(B3),Glu(B29)-insulin After Intravenous Administration to Rabbits

| Time [h] | Human insulin | Lys(B3),Glu(B29)-insulin |
|---|---|---|
| 0 | 100 | 100 |
| 0.25 | 89.17 | 89.47 |
| 0.5 | 67.56 | 58.32 |
| 0.75 | 73.24 | 66.59 |
| 1 | 73.13 | 68.21 |
| 1.5 | 78.12 | 71.95 |
| 2 | 89.47 | 80.88 |
| 3 | 107.01 | 94.2 |
| 4 | 104.55 | 99.78 |

8 rabbits received the indicated insulins intravenously (0.2 IU/kg). In the course of the following four hours, the blood glucose concentration was determined at the times indicated and calculated in % of the starting value at time 0. The mean values show no significant differences in the biological activity between human insulin and Lys(B3),Glu(B29)-insulin.

Example 7

Biological Activity of Lys(B3),Ile(B27)- and Lys(B3),Ile(B28)-insulin After Intravenous Administration to Rabbits 6 rabbits received the indicated insulins intravenously (0.2 IU/kg). In the course of the following four hours, the blood glucose concentration was determined at the times indicated and calculated in % of the starting value at time 0. The mean values show no significant differences in the biological activity between human insulin, Lys(B3),Ile(B27)- and Lys(B3),Ile(B28)-insulin.

| Time [h] | H insulin | Lys(B3),Ile(B27)-insulin | Lys(B3),Ile(B28)-insulin |
|---|---|---|---|
| 0 | 100 | 100 | 100 |
| 0.33 | 67.8 | 62.6 | 63.3 |
| 0.66 | 54.9 | 60.6 | 55.8 |
| 1 | 55.2 | 66.8 | 59.3 |
| 1.5 | 63 | 79.2 | 66.7 |
| 2 | 77.8 | 90.9 | 81.6 |
| 3 | 91.5 | 96.3 | 97.2 |
| 4 | 99.5 | 96 | 101.6 |

Example 8

Pharmacodynamics of Lys(B3),Glu(B29)-insulin and Lys(B3), le(B28)-insulin after Subcutaneous Administration to Dogs Four dogs in each case received subcutaneous injections of the indicated insulins (0.3 IU/kg). The blood glucose was kept at 3.7 to 4 mmol/l by continuous infusion of glucose. The mean glucose infusion rate±SEM from the time of injection (t=0) through 240 minutes is shown.

GLUCOSE CLAMP IN FASTING DOGS WITH RAPIDLY ACTING INSULIN DERIVATIVES
Characteristics of the glucose infusion profiles
Dose: 1 x 0.3 IU/kg s.c at $t_0$ (n = 4)

| | Increment phase | | | Decrement phase | |
|---|---|---|---|---|---|
| Preparation | Inflection point (min) | Slope of the inflection point | $t_{max}$ (min) | Inflection point (min) | Slope of the inflection point |
| H. insulin, Hoechst | 43 | 0.144 | 100 | 156 | −0.065 |
| Lys(B3), Glu(B29) insulin | 33 | 0.227 | 80 | 127 | −0.091 |
| Lys(B3), Ile(B28) insulin | 16 | 0.267 | 60 | 104 | −0.102 |

GLUCOSE CLAMP IN FASTING DOGS WITH RAPIDLY ACTING INSULIN DERIVATIVES
Dose: 1 x 0.3 IU/kg s.c at $t_0$ (mean ± sem, n = 4)

| H. insulin, Hoechst | | | | | | Lys (B3), Glu (B29) -Insulin | | | | | | Lys (B3), Ile (B28)-Insulin | | | | | |
|---|---|---|---|---|---|---|---|---|---|---|---|---|---|---|---|---|---|
| Glucose infusion rate | | | Blood glucose | | | Glucose infusion rate | | | Blood glucose | | | Glucose infusion rate | | | Blood glucose | | |
| Time | mg·min⁻¹·kg⁻¹ | | Time | mmol/l | | Time | mg·min⁻¹·kg⁻¹ | | Time | mmol/l | | Time | mg·min⁻¹·kg⁻¹ | | Time | mmol/l | |
| min | mean | sem | min | mean | sem | min | mean | sem | min | mean | sem | min | mean | sem | min | mean | sem |
| 0 | 0.00 | 0.00 | 0 | 3.98 | 0.07 | 0 | 0.00 | 0.00 | 0 | 3.77 | 0.12 | 0 | 0.00 | 0.00 | 0 | 3.74 | 0.07 |
| 6 | 0.14 | 0.01 | 4 | 3.97 | 0.04 | 6 | 0.24 | 0.08 | 5 | 3.85 | 0.22 | 6 | 1.54 | 0.53 | 4 | 3.60 | 0.17 |
| 11 | 0.23 | 0.08 | 9 | 3.98 | 0.08 | 11 | 0.36 | 0.18 | 10 | 3.86 | 0.17 | 11 | 3.75 | 1.24 | 10 | 3.49 | 0.19 |
| 16 | 0.35 | 0.19 | 14 | 3.99 | 0.04 | 16 | 0.95 | 0.60 | 15 | 3.86 | 0.22 | 16 | 5.25 | 0.89 | 15 | 3.53 | 0.14 |
| 21 | 0.44 | 0.18 | 19 | 4.01 | 0.05 | 21 | 2.75 | 0.96 | 20 | 3.61 | 0.16 | 21 | 8.25 | 1.67 | 20 | 3.38 | 0.18 |
| 26 | 1.50 | 0.25 | 24 | 3.85 | 0.08 | 26 | 3.25 | 0.65 | 25 | 3.73 | 0.14 | 26 | 7.25 | 1.63 | 25 | 3.81 | 0.20 |
| 31 | 3.50 | 0.56 | 29 | 3.82 | 0.13 | 31 | 3.75 | 0.22 | 30 | 3.76 | 0.08 | 31 | 7.50 | 1.25 | 30 | 3.64 | 0.13 |
| 36 | 5.50 | 0.90 | 34 | 3.77 | 0.13 | 36 | 5.25 | 0.41 | 35 | 3.66 | 0.15 | 36 | 8.50 | 1.15 | 35 | 3.65 | 0.12 |

-continued

GLUCOSE CLAMP IN FASTING DOGS WITH RAPIDLY ACTING INSULIN DERIVATIVES

Dose: 1 × 0.3 IU/kg s.c. at $t_0$ (mean ± sem, n = 4)

| H. insulin, Hoechst | | | | | | Lys (B3), Glu (B29)-Insulin | | | | | | Lys (B3), Ile (B28)-Insulin | | | | | |
|---|---|---|---|---|---|---|---|---|---|---|---|---|---|---|---|---|---|
| Glucose infusion rate | | | Blood glucose | | | Glucose infusion rate | | | Blood glucose | | | Glucose infusion rate | | | Blood glucose | | |
| Time | mg·min$^{-1}$·kg$^{-1}$ | | Time | mmol/l | | Time | mg·min$^{-1}$·kg$^{-1}$ | | Time | mmol/l | | Time | mg·min$^{-1}$·kg$^{-1}$ | | Time | mmol/l | |
| min | mean | sem | min | mean | sem | min | mean | sem | min | mean | sem | min | mean | sem | min | mean | sem |
| 41 | 4.50 | 0.56 | 39 | 3.99 | 0.07 | 41 | 6.00 | 0.00 | 40 | 3.71 | 0.12 | 41 | 11.00 | 1.12 | 40 | 3.63 | 0.09 |
| 46 | 4.00 | 1.17 | 44 | 4.09 | 0.11 | 46 | 9.00 | 0.87 | 45 | 3.58 | 0.19 | 46 | 11.75 | 0.22 | 45 | 3.68 | 0.10 |
| 51 | 5.25 | 0.54 | 49 | 3.98 | 0.06 | 51 | 8.00 | 0.00 | 50 | 3.73 | 0.14 | 51 | 10.75 | 0.96 | 50 | 3.81 | 0.09 |
| 56 | 5.75 | 0.89 | 54 | 4.01 | 0.10 | 56 | 8.50 | 0.56 | 55 | 3.81 | 0.11 | 56 | 11.25 | 1.78 | 55 | 3.73 | 0.11 |
| 61 | 7.25 | 1.19 | 59 | 3.93 | 0.13 | 61 | 11.50 | 0.43 | 60 | 3.57 | 0.14 | 61 | 10.50 | 1.09 | 60 | 3.78 | 0.16 |
| 66 | 6.50 | 1.09 | 64 | 4.08 | 0.06 | 67 | 10.00 | 1.22 | 65 | 3.81 | 0.20 | 66 | 9.75 | 1.85 | 65 | 3.83 | 0.14 |
| 71 | 7.75 | 1.08 | 69 | 3.98 | 0.01 | 71 | 11.50 | 0.43 | 70 | 3.85 | 0.23 | 71 | 11.00 | 1.50 | 70 | 3.69 | 0.11 |
| 76 | 7.75 | 1.14 | 74 | 4.08 | 0.10 | 76 | 11.00 | 1.70 | 75 | 3.81 | 0.28 | 76 | 10.50 | 0.83 | 75 | 3.81 | 0.06 |
| 81 | 8.50 | 1.09 | 79 | 4.03 | 0.12 | 81 | 10.50 | 0.83 | 80 | 3.94 | 0.15 | 81 | 9.25 | 1.19 | 80 | 3.89 | 0.01 |
| 86 | 8.75 | 1.29 | 84 | 4.09 | 0.15 | 86 | 8.25 | 1.75 | 85 | 3.95 | 0.18 | 86 | 10.00 | 1.22 | 85 | 3.78 | 0.02 |
| 91 | 8.75 | 1.08 | 89 | 4.03 | 0.18 | 91 | 9.00 | 0.50 | 90 | 3.69 | 0.12 | 91 | 8.75 | 1.29 | 90 | 3.83 | 0.04 |
| 96 | 9.25 | 2.33 | 94 | 3.99 | 0.22 | 96 | 11.00 | 0.94 | 95 | 3.56 | 0.14 | 96 | 10.25 | 0.74 | 95 | 3.67 | 0.11 |
| 101 | 8.50 | 1.68 | 99 | 4.08 | 0.10 | 101 | 9.75 | 0.41 | 100 | 3.71 | 0.16 | 101 | 10.00 | 1.22 | 100 | 3.66 | 0.18 |
| 106 | 8.50 | 1.44 | 104 | 3.96 | 0.08 | 106 | 10.25 | 0.89 | 105 | 3.59 | 0.20 | 106 | 10.50 | 1.15 | 105 | 3.59 | 0.15 |
| 111 | 8.00 | 1.06 | 109 | 3.92 | 0.19 | 111 | 8.00 | 0.94 | 110 | 3.84 | 0.16 | 111 | 8.50 | 1.03 | 109 | 3.74 | 0.10 |
| 116 | 9.25 | 1.47 | 114 | 3.83 | 0.17 | 116 | 10.25 | 0.74 | 115 | 3.40 | 0.10 | 116 | 7.75 | 0.22 | 115 | 3.81 | 0.08 |
| 121 | 8.00 | 1.58 | 119 | 4.04 | 0.21 | 121 | 10.25 | 1.24 | 120 | 3.58 | 0.25 | 121 | 7.50 | 1.09 | 120 | 3.83 | 0.07 |
| 126 | 8.00 | 1.37 | 124 | 3.95 | 0.12 | 126 | 9.75 | 1.34 | 125 | 3.70 | 0.23 | 126 | 6.00 | 1.62 | 125 | 3.94 | 0.07 |
| 131 | 9.25 | 1.19 | 129 | 3.81 | 0.09 | 131 | 7.75 | 1.52 | 130 | 3.88 | 0.21 | 131 | 4.25 | 1.29 | 130 | 3.95 | 0.12 |
| 136 | 8.50 | 1.30 | 134 | 3.92 | 0.16 | 136 | 5.50 | 1.44 | 135 | 3.97 | 0.15 | 136 | 5.33 | 1.19 | 135 | 3.70 | 0.20 |
| 141 | 8.50 | 1.25 | 139 | 3.86 | 0.13 | 141 | 6.75 | 1.85 | 140 | 3.64 | 0.15 | 142 | 4.75 | 1.19 | 140 | 3.71 | 0.08 |
| 146 | 8.25 | 1.24 | 144 | 3.91 | 0.12 | 146 | 6.25 | 1.67 | 145 | 3.71 | 0.14 | 146 | 4.00 | 0.94 | 145 | 3.73 | 0.07 |
| 151 | 7.00 | 1.46 | 149 | 4.06 | 0.08 | 151 | 4.75 | 1.14 | 150 | 3.82 | 0.08 | 151 | 3.25 | 0.89 | 150 | 3.74 | 0.14 |
| 156 | 6.25 | 1.29 | 154 | 4.05 | 0.04 | 156 | 5.75 | 0.96 | 155 | 3.71 | 0.11 | 156 | 4.00 | 0.71 | 155 | 3.62 | 0.05 |
| 161 | 6.00 | 0.79 | 159 | 3.97 | 0.12 | 161 | 4.75 | 0.82 | 160 | 3.81 | 0.11 | 162 | 3.75 | 0.54 | 160 | 3.69 | 0.09 |
| 166 | 5.00 | 0.50 | 164 | 4.04 | 0.09 | 166 | 5.50 | 1.03 | 165 | 3.67 | 0.15 | 166 | 2.25 | 0.54 | 165 | 3.80 | 0.13 |
| 171 | 4.75 | 1.39 | 169 | 3.95 | 0.15 | 171 | 4.75 | 0.41 | 169 | 3.81 | 0.04 | 171 | 2.25 | 0.41 | 170 | 3.75 | 0.05 |
| 176 | 4.33 | 0.54 | 174 | 4.01 | 0.12 | 176 | 3.75 | 0.54 | 175 | 3.83 | 0.08 | 176 | 1.63 | 0.48 | 175 | 3.77 | 0.05 |
| 181 | 5.33 | 1.19 | 179 | 3.88 | 0.14 | 181 | 4.00 | 0.94 | 180 | 3.75 | 0.16 | 181 | 1.54 | 0.53 | 180 | 3.77 | 0.12 |
| 186 | 4.67 | 0.72 | 184 | 4.03 | 0.09 | 186 | 2.88 | 0.87 | 185 | 3.85 | 0.14 | 186 | 0.88 | 0.46 | 185 | 3.76 | 0.10 |
| 191 | 3.33 | 0.72 | 189 | 4.12 | 0.11 | 191 | 3.25 | 0.41 | 190 | 3.78 | 0.10 | 191 | 1.19 | 0.54 | 190 | 3.76 | 0.04 |
| 196 | 3.00 | 0.00 | 194 | 4.13 | 0.03 | 196 | 3.13 | 0.84 | 195 | 3.81 | 0.14 | 196 | 1.28 | 0.79 | 195 | 3.76 | 0.08 |
| 201 | 3.67 | 0.72 | 199 | 3.98 | 0.11 | 201 | 2.13 | 0.51 | 200 | 3.88 | 0.13 | 202 | 1.07 | 0.58 | 200 | 3.71 | 0.11 |
| 206 | 4.67 | 0.72 | 204 | 3.91 | 0.05 | 206 | 2.06 | 0.66 | 205 | 3.85 | 0.14 | 206 | 0.94 | 0.60 | 205 | 3.66 | 0.08 |
| 211 | 4.67 | 0.72 | 209 | 3.92 | 0.08 | 211 | 1.79 | 0.62 | 210 | 3.85 | 0.17 | 212 | 1.41 | 1.04 | 210 | 3.69 | 0.08 |
| 216 | 3.33 | 0.72 | 214 | 4.09 | 0.04 | 216 | 1.78 | 0.63 | 215 | 3.85 | 0.18 | 217 | 0.95 | 0.60 | 215 | 3.74 | 0.09 |
| 221 | 3.00 | 0.94 | 219 | 4.05 | 0.11 | 221 | 1.41 | 0.58 | 220 | 3.87 | 0.16 | 221 | 0.54 | 0.21 | 220 | 3.66 | 0.17 |
| 226 | 2.17 | 0.68 | 224 | 4.17 | 0.12 | 226 | 0.78 | 0.36 | 225 | 3.85 | 0.13 | 226 | 0.72 | 0.38 | 225 | 3.72 | 0.10 |
| 231 | 2.67 | 0.98 | 229 | 4.00 | 0.13 | 231 | 0.85 | 0.37 | 230 | 3.72 | 0.23 | 231 | 0.69 | 0.38 | 230 | 3.75 | 0.08 |
| 236 | 2.00 | 0.47 | 234 | 4.01 | 0.05 | 236 | 0.76 | 0.51 | 235 | 3.74 | 0.21 | 237 | 0.94 | 0.60 | 235 | 3.71 | 0.03 |
| 240 | 1.17 | 0.36 | 239 | 4.08 | 0.02 | 240 | 1.07 | 0.47 | 240 | 3.56 | 0.18 | 240 | 0.88 | 0.61 | 240 | 3.69 | 0.03 |

What is claimed is:

1. An insulin derivative or a physiologically tolerable salt thereof, in which asparagine (Asn) in position B3 of the B chain is replaced by a naturally occurring basic amino acid residue and at least one amino acid residue in the positions B27, B28 or B29 of the B chain is replaced by another naturally occurring neutral or acidic amino acid residue.

2. An insulin derivative or a physiologically tolerable salt thereof as claimed in claim 1, of formula I $$
\begin{array}{c}
\text{S}\text{———}\text{S} \\
| \quad\quad\quad | \\
\text{(A1-A5)-Cys-Cys-A8-A9-A10-Cys-(A12-A19)-Cys-A21} \\
| \quad\quad\quad\quad\quad\quad\quad\quad | \\
\text{S——S} \quad\quad \text{S———S} \\
| \quad\quad\quad\quad\quad\quad\quad | \\
\text{B1-Val-B3-Glu-His-Leu-Cys-(B8-B18)-Cys-(B20-B26)-B27-B28-B29-B30,}
\end{array}
$$

in which (A1–A5) are the amino acid residues in the positions A1 to A5 of the A chain of human insulin or animal insulin, (A12–A19) are the amino acid residues in the positions A12 to A19 of the A chain of human insulin or animal insulin, A21 is Asn, Asp, Gly, Ser, Thr or Ala, (B8–B18) are the amino acid residues in the positions B8 to B18 of the B chain of human insulin or animal insulin, (B20–B26) are the amino acid residues in the positions B20 to B26 of the B chain of human insulin or animal insulin, A8, A9, A10 are the amino acid residues in the positions A8, A9 and A10 of the A chain of human insulin or animal insulin, B30 is —OH or the amino acid residue in position B30 of the B chain of human insulin or animal insulin, B1 is a phenylalanine residue (Phe) or a hydrogen atom, B3 is a naturally occurring basic amino acid residue, B27, B28 and B29 are the amino acid residues in the positions B27, B28 and B29 of the B chain of human insulin or animal insulin or in each case are another naturally occurring amino acid residue, where at least one of the amino acid residues in the positions B27, B28 and B29 of the B chain is replaced by another naturally occurring amino acid residue which is selected from the group consisting of the neutral or acidic amino acids.

3. An insulin derivative or a physiologically tolerable salt thereof as claimed in claim 2, wherein
   A8 is alanine (Ala),
   A9 is serine (Ser),
   A10 is valine (Val) and
   B30 is alanine (Ala).
4. An insulin derivative or a physiologically tolerable salt thereof as claimed in claim 2, wherein
   A8 is threonine (Thr),
   A9 is serine (Ser) and
   A10 is isoleucine (Ile).
5. An insulin derivative or a physiologically tolerable salt thereof as claimed in claim 4, wherein
   B30 is alanine (Ala).
6. An insulin derivative or a physiologically tolerable salt thereof as claimed in claim 4, wherein
   B30 is threonine (Thr).
7. An insulin derivative or a physiologically tolerable salt thereof as claimed in claim 6, wherein
   (A1–A5) are the amino acid residues in the positions A1 to A5 of the A chain of human insulin,
   (A12–A19) are the amino acid residues in the positions A12 to A19 of the A chain of human insulin,
   (B8–B18) are the amino acid residues in the positions B8 to B18 of the B chain of human insulin and
   (B20–B26) are the amino acid residues in the positions B20 to B26 of the B chain of human insulin.
8. An insulin derivative or a physiologically tolerable salt thereof as claimed in claim 1, wherein the amino acid residue in position B1 of the B chain is a phenylalanine residue (Phe).
9. An insulin derivative or a physiologically tolerable salt thereof as claimed in claim 1, wherein the amino acid residue in position B3 of the B chain is a histidine (His), lysine (Lys) or arginine residue (Arg).
10. An insulin derivative or a physiologically tolerable salt thereof as claimed in claim 9, wherein the amino acid residue in position B3 of the B chain is a histidine residue (His).
11. An insulin derivative or a physiologically tolerable salt thereof as claimed in claim 9, wherein the amino acid residue in position B3 of the B chain is an arginine residue (Arg).
12. An insulin derivative or a physiologically tolerable salt thereof as claimed in claim 9, wherein the amino acid residue in position B3 of the B chain is a lysine residue (Lys).
13. An insulin derivative or a physiologically tolerable salt thereof as claimed in claim 1, wherein at least one of the amino acid residues in the positions B27, B28 and B29 of the B chain is a naturally occurring amino acid residue which is selected from the group consisting of isoleucine (Ile), aspartic acid (Asp) and glutamic acid (Glu).
14. An insulin derivative or a physiologically tolerable salt thereof as claimed in claim 1, wherein at least one of the amino acid residues in the positions B27, B28 and B29 of the B chain is a naturally occurring amino acid residue which is selected from the group consisting of the acidic amino acids.
15. An insulin derivative or a physiologically tolerable salt thereof as claimed in claim 14, wherein at least one of the amino acid residues in the positions B27, B28 and B29 of the B chain is an aspartic acid residue (Asp).
16. An insulin derivative or a physiologically tolerable salt thereof as claimed in claim 15, wherein the amino acid residue in position B27 of the B chain is an aspartic acid residue (Asp).
17. An insulin derivative or a physiologically tolerable salt thereof as claimed in claim 15, wherein the amino acid residue in position B28 of the B chain is an aspartic acid residue (Asp).
18. An insulin derivative or a physiologically tolerable salt thereof as claimed in claim 15, wherein the amino acid residue in position B29 of the B chain is an aspartic acid residue (Asp).
19. An insulin derivative or a physiologically tolerable salt thereof as claimed in claim 14, wherein at least one of the amino acid residues in the positions B27, B28 and B29 of the B chain is a glutamic acid residue (Glu).
20. An insulin derivative or a physiologically tolerable salt thereof as claimed in claim 19, wherein the amino acid residue in position B27 of the B chain is a glutamic acid residue (Glu).
21. An insulin derivative or a physiologically tolerable salt thereof as claimed in claim 19, wherein the amino acid residue in position B28 of the B chain is a glutamic acid residue (Glu).
22. An insulin derivative or a physiologically tolerable salt thereof as claimed in claim 19, wherein the amino acid residue in position B29 of the B chain is a glutamic acid residue (Glu).
23. An insulin derivative or a physiologically tolerable salt thereof as claimed in claim 22, wherein the B chain has the sequence
   Phe Val Lys Gln His Leu Cys Gly Ser His Leu Val Glu Ala Leu Tyr Leu Val Cys Gly Glu Arg Gly Phe Phe Tyr Thr Pro Glu Thr (SEQ ID NO 3).
24. A process for the preparation of an insulin derivative as claimed in claim 23, comprising
   a) constructing a replicable expression vehicle which contains a DNA sequence which codes for a precursor of the insulin derivative, in which the amino acid residue in position A1 of the A chain is linked to the amino acid residue B30 of the B chain via a peptide chain of the formula II

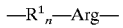   II in which $R^1_n$ is a peptide chain having n amino acid residues and n is an integer from 0 to 34, and the B chain is modified by covalent linkage of the amino acid at position B1 to a peptide chain of the formula III

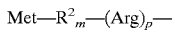   III in which $R^2_m$ is a peptide chain having m amino acid residues, m is an integer from 0 to 40 and p is 0, 1 or 2,
   b) expressing the DNA sequence which codes for a precursor of the insulin derivative in a host cell, and
   c) releasing the insulin derivative from its precursor using chemical and/or enzymatic methods, wherein the precursor of the insulin derivative has the sequence
   Met Ala Thr Thr Ser Thr Gly Asn Ser Ala Arg Phe Val Lys Gln His Leu Cys Gly Ser His Leu Val Glu Ala Leu Tyr Leu Val Cys Gly Glu Arg Gly Phe Phe Tyr Thr Pro Glu Thr Arg Arg Glu Ala Glu Asp Pro Gln Val Gly Gln Val Glu Leu Gly Gly Gly Pro Gly Ala Gly Ser Leu Gln Pro Leu Ala Leu Glu Gly Ser Leu Gln Lys Arg Gly Ile Val Glu Gln Cys Cys Thr Ser Ile Cys Ser Leu Tyr Gln Leu Glu Asn Tyr Cys Asn (SEQ ID NO.: 6).
25. An insulin derivative or a physiologically tolerable salt thereof as claimed in claim 1, wherein at least one of the amino acid residues in the positions B27 and B28 of the B chain is replaced by a naturally occurring amino acid residue which is selected from the group consisting of the neutral amino acids.

26. An insulin derivative or a physiologically tolerable salt thereof as claimed in claim 25, wherein at least one of the amino acid residues in the positions B27, B28 and B29 of the B chain is an isoleucine residue (Ile).

27. An insulin derivative or a physiologically tolerable salt thereof as claimed in claim 26, wherein the amino acid residue in position B28 of the B chain is an isoleucine residue (Ile).

28. An insulin derivative or a physiologically tolerable salt thereof as claimed in claim 27, wherein the B chain has the sequence Phe Val Lys Gln His Leu Cys Gly Ser His Leu Val Glu Ala Leu Tyr Leu Val Cys Gly Glu Arg Gly Phe Phe Tyr Thr Ile Lys Thr (SEQ ID NO 4).

29. A process for the preparation of an insulin derivative as claimed in claim 28, comprising
   a) constructing a replicable expression vehicle which contains a DNA sequence which codes for a precursor of the insulin derivative, in which the amino acid residue in position A1 of the A chain is linked to the amino acid residue B30 of the B chain via a peptide chain of the formula II $$—R^1{}_n—Arg—$$   II in which $R^1{}_n$ is a peptide chain having n amino acid residues and n is an integer from 0 to 34, and the B chain is modified by covalent linkage of the amino acid at position B1 to a peptide chain of the formula III $$Met—R^2{}_m—(Arg)_p—$$   III in which $R^2{}_m$ is a peptide chain having m amino acid residues, m is an integer from 0 to 40 and p is 0, 1 or 2,
   b) expressing the DNA sequence which codes for a precursor of the insulin derivative in a host cell, and
   c) releasing the insulin derivative from its precursor using chemical and/or enzymatic methods, wherein the precursor of the insulin derivative has the sequence
      Met Ala Thr Thr Ser Thr Gly Asn Ser Ala Arg Phe Val Lys Gln His Leu Cys Gly Ser His Leu Val Glu Ala Leu Tyr Leu Val Cys Gly Glu Arg Gly Phe Phe Tyr Thr Ile Lys Thr Arg Arg Glu Ala Glu Asp Pro Gln Val Gly Gln Val Glu Leu Gly Gly Gly Pro Gly Ala Gly Ser Leu Gln Pro Leu Ala Leu Glu Gly Ser Leu Gln Lys Arg Gly Ile Val Glu Gln Cys Cys Thr Ser Ile Cys Ser Leu Tyr Gln Leu Glu Asn Tyr Cys Asn (SEQ ID NO.: 7).

30. An insulin derivative or a physiologically tolerable salt thereof as claimed in claim 26, wherein the amino acid residue in position B27 of the B chain is an isoleucine residue (Ile).

31. An insulin derivative or a physiologically tolerable salt thereof as claimed in claim 30, wherein the B chain has the sequence Phe Val Lys Gln His Leu Cys Gly Ser His Leu Val Glu Ala Leu Tyr Leu Val Cys Gly Glu Arg Gly Phe Phe Tyr Ile Pro Lys Thr (SEQ ID NO 5).

32. A process for the preparation of an insulin derivative as claimed in claim 31, comprising
   a) constructing a replicable expression vehicle which contains a DNA sequence which codes for a precursor of the insulin derivative, in which the amino acid residue in position A1 of the A chain is linked to the amino acid residue B30 of the B chain via a peptide chain of the formula II $$—R^1{}_n—Arg—$$   II in which $R^1{}_n$ is a peptide chain having n amino acid residues and n is an integer from 0 to 34, and the B chain is modified by covalent linkage of the amino acid at position B1 to a peptide chain of the formula III $$Met—R^2{}_m—(Arg)_p—$$   III in which $R^2{}_m$ is a peptide chain having m amino acid residues, m is an integer from 0 to 40 and p is 0, 1 or 2,
   b) expressing the DNA sequence which codes for a precursor of the insulin derivative in a host cell, and
   c) releasing the insulin derivative from its precursor using chemical and/or enzymatic methods, wherein the precursor of the insulin derivative has the sequence
      Met Ala Thr Thr Ser Thr Gly Asn Ser Ala Arg Phe Val Lys Gln His Leu Cys Gly Ser His Leu Val Glu Ala Leu Tyr Leu Val Cys Gly Glu Arg Gly Phe Phe Tyr Ile Pro Lys Thr Arg Arg Glu Ala Glu Asp Pro Gln Val Gly Gln Val Glu Leu Gly Gly Gly Pro Gly Ala Gly Ser Leu Gln Pro Leu Ala Leu Glu Gly Ser Leu Gln Lys Arg Gly Ile Val Glu Gln Cys Cys Thr Ser Ile Cys Ser Leu Tyr Gln Leu Glu Asn Tyr Cys Asn (SEQ ID NO.: 8).

33. An insulin derivative or a physiologically tolerable salt thereof as claimed in claim 1, wherein the amino acid residue in position A21 of the A chain is an asparagine residue (Asp).

34. An insulin derivative or a physiologically tolerable salt thereof as claimed in claim 33, wherein the A chain has the sequence Gly Ile Val Glu Gln Cys Cys Thr Ser Ile Cys Ser Leu Tyr Gln Leu Glu Asn Tyr Cys Asp (SEQ ID NO.: 9)
and the B chain has the sequence Phe Val Lys Gln His Leu Cys Gly Ser His Leu Val Glu Ala Leu Tyr Leu Val Cys Gly Glu Arg Gly Phe Phe Tyr Thr Ile Lys Thr (SEQ ID NO.: 10).

35. A process for the preparation of an insulin derivative as claimed in claim 33, comprising
   a) constricting a replicable, expression vehicle which contains a DNA sequence which codes for a precursor of the insulin derivative, in which the amino acid residue in position A1 of the A chain is linked to the amino acid residue B30 of the B chain via a peptide chain of the formula II $$—R^1{}_n—Arg—$$   II in which $R^1{}_n$ is a peptide chain having n amino acid residues and n is an integer from 0 to 34, and the B chain is modified by covalent linkage of the amino acid at position B1 to a peptide chain of the formula III $$Met—R^2{}_m—(Arg)_p—$$   III in which $R^2{}_m$ is a peptide chain having m amino acid residues, m is an integer from 0 to 40 and p is 0, 1 or 2,
   b) expressing the DNA sequence which codes for a precursor of the insulin derivative in a host cell, and c) releasing the insulin derivative from its precursor using chemical and/or enzymatic methods, wherein the precursor of the insulin derivative has the sequence
Met Ala Thr Thr Ser Thr Gly Asn Ser Ala Arg Phe Val Lys Gln His Leu Cys Gly Ser His Leu Val Glu Ala Leu Tyr Leu Val Cys Gly Glu Arg Gly Phe Phe Tyr Thr Ile Lys Thr Arg Arg Glu Ala Glu Asp Pro Gln Val Gly Gln Val Glu Leu Gly Gly Gly Pro Gly Ala Gly Ser Leu Gln Pro Leu Ala Leu Glu Gly Ser Leu Gln Lys Arg Gly Ile Val Glu Gln Cys Cys Thr Ser Ile Cys Ser Leu Tyr Gln Leu Glu Asn Tyr Cys Asp (SEQ ID No.: 11).

36. A pharmaceutical preparation, which comprises at least one insulin derivative and/or a physiologically tolerable salt thereof as claimed in claim 1.

37. A pharmaceutical preparation as claimed in claim 36, which comprises the insulin derivative and/or the physiologically tolerable salt thereof in dissolved, amorphous and/or crystalline form.

38. A pharmaceutical preparation as claimed in claim 36, which further comprises a depot auxiliary.

39. A pharmaceutical preparation as claimed in claim 38, wherein the depot auxiliary is protamine sulfate, where the insulin derivative and/or the physiologically tolerable salt thereof is present with the protamine sulfate in a cocrystallizate.

40. A method for the treatment of diabetes mellitus comprising administering an effective amount of the pharmaceutical preparation of claim 36.

41. An injectable solution having insulin activity, comprising the pharmaceutical preparation as claimed in claim 36 in dissolved form.

42. An insulin derivative or a physiologically tolerable salt thereof as claimed in claim 1, wherein asparagine (Asn) in position 21 of the A chain is replaced by Asp, Gly, Ser, Thr or Ala.

43. An insulin derivative or a physiologically tolerable salt thereof as claimed in claim 1, wherein phenylalanine (Phe) in position B1 of the B chain is absent.

44. An insulin derivative or a physiologically tolerable salt thereof as claimed in claim 1, wherein the amino acid residue in position B30 of the B chain is absent.

45. A process for the preparation of an insulin derivative or of a physiologically tolerable salt thereof as claimed in claim 1, comprising
a) constructing a replicable, expression vehicle which contains a DNA sequence which codes for a precursor of the insulin derivative, in which the amino acid residue in position A1 of the A chain is linked to the amino acid residue B30 of the B chain via a peptide chain of the formula II —$R^1_n$–Arg—  II in which $R^1_n$ is a peptide chain having n amino acid residues and n is an integer from 0 to 34, and the B chain is modified by covalent linkage of the amino acid at position B1 to a peptide chain of the formula III Met—$R^2_m$–(Arg)$_p$–  III in which $R^2_m$ is a peptide chain having m amino acid residues, m is an integer from 0 to 40 and p is 0, 1 or 2,
b) expressing the DNA sequence which codes for a precursor of the insulin derivative in a host cell, and
c) releasing the insulin derivative from its precursor using chemical and/or enzymatic methods.

46. The process as claimed in claim 45, wherein the host cell is a bacterium.

47. The process as claimed in claim 46, wherein the bacterium is *E. coli*.

48. The process as claimed in claim 45, wherein the host cell is a yeast.

49. The process as claimed in claim 48, wherein the yeast is *Saccharomyces cerevisiae*.

50. A precursor of an insulin derivative, wherein the precursor has a sequence selected from the group consisting of SEQ ID NO.: 11, SEQ ID NO.:6, SEQ ID NO.:8, and SEQ ID NO.:7.

51. The precursor of claim 50, wherein the precursor has the sequence of SEQ ID NO.:6.

52. The precursor of claim 50, wherein the precursor has the sequence of SEQ ID NO.:8.

53. The precursor of claim 50, wherein the precursor has the sequence of SEQ ID NO.:7.

54. The precursor of claim 50, wherein the precursor has the sequence of SEQ ID NO.:11.

55. An isolated or purified nucleic acid comprising a sequence which codes for a precursor of an insulin derivative having a sequence selected from the group consisting of SEQ ID NO.:11, SEQ ID NO.:6, SEQ ID NO.8, and SEQ ID NO.:7.

56. The isolated or purified nucleic acid of claim 55, having the sequence of SEQ ID NO.11.

57. An expression vehicle comprising a nucleic acid as claimed in claim 56.

58. A host cell which is transformed using an expression vehicle as claimed in claim 57.

59. The isolated or purified nucleic acid of claim 55, having the sequence of SEQ ID NO.:6.

60. An expression vehicle comprising a nucleic acid as claimed in claim 59.

61. The isolated or purified nucleic acid of claim 55, having the sequence of SEQ ID NO.:8.

62. An expression vehicle comprising a nucleic acid as claimed in claim 61.

63. The isolated or purified nucleic acid of claim 55, having the sequence of SEQ ID NO.:7.

64. An expression vehicle comprising a nucleic acid as claimed in claim 63.

* * * * *

UNITED STATES PATENT AND TRADEMARK OFFICE
CERTIFICATE OF CORRECTION

PATENT NO. : 6,221,633 B1
DATED : April 24, 2001
INVENTOR(S) : Johann Ertl et al.

It is certified that error appears in the above-identified patent and that said Letters Patent is hereby corrected as shown below:

Column 26, claim 32,
Line 30, "Lcu" should read -- Leu --.

Column 26, claim 35,
Line 47, "constricting" should read -- constructing --.

Signed and Sealed this

Fifth Day of March, 2002

*Attest:*

*Attesting Officer*

JAMES E. ROGAN
*Director of the United States Patent and Trademark Office*

UNITED STATES PATENT AND TRADEMARK OFFICE
CERTIFICATE OF CORRECTION

| | |
|---|---|
| PATENT NO. | : 6,221,633 C1 |
| APPLICATION NO. | : 09/099307 |
| DATED | : May 22, 2007 |
| INVENTOR(S) | : Johann Ertl et al. |

It is certified that error appears in the above-identified patent and that said Letters Patent is hereby corrected as shown below:

Column 1, lines 31-35, "(A1-A5) are the amino acid residues in the positions A1 to A5 of the A chain of human insulin [or animal insulin]," should read --(A1-A5) are the amino acid residues in the position A1 to A5 of the A chain of human insulin or animal insulin,--.

Column 2, after line 26, please insert

--in which
      (A1-A5) are the amino acid residues in the positions A1 to A5 of the A chain of human insulin [or animal insulin],
      (A12-A19) are the amino acid residues in the positions A12 to A19 of the A chain of human insulin or animal insulin,
      A21 is Asn, Asp, Gly, Ser, Thr, or Ala,
      (B8 - B18) are the amino acid residues in the positions B8 to B18 of the B chain of human insulin or animal insulin,
      (B20-B26) are the amino acid residues in the positions B20 to B26 of the B chain of human insulin or animal insulin,
      A8, A9, A10 are the amino acid residues in the positions A8, A9, and A10 of the A chain of human insulin or animal insulin,
      B30 is -OH or the amino acid residue in portion B30 of the B chain of human insulin or animal insulin,
      B1 is a phenylalanine residue (Phe) or a hydrogen atom,
      B3 is a naturally occurring basic amino acid residue,

UNITED STATES PATENT AND TRADEMARK OFFICE
CERTIFICATE OF CORRECTION

PATENT NO. : 6,221,633 C1
APPLICATION NO. : 09/099307
DATED : May 22, 2007
INVENTOR(S) : Johann Ertl et al.

It is certified that error appears in the above-identified patent and that said Letters Patent is hereby corrected as shown below:

B27, B28 and B29 are the amino acid residues in the positions B27, B28, B29 of the B chain of human insulin or animal insulin, or in each case are another naturally occurring amino acid residue, where at least one of the amino acid residues in the positions B27, B28, and B29 of the B chain is replaced by another naturally occurring amino acid residue which is selected from the group consisting of the neutral or acidic amino acids.

Signed and Sealed this

Twenty-third Day of October, 2007

JON W. DUDAS
*Director of the United States Patent and Trademark Office*

UNITED STATES PATENT AND TRADEMARK OFFICE
CERTIFICATE OF CORRECTION

| | | |
|---|---|---|
| PATENT NO. | : 6,221,633 C1 | |
| APPLICATION NO. | : 90/006928 | |
| DATED | : May 22, 2007 | |
| INVENTOR(S) | : Johann Ertl et al. | |

It is certified that error appears in the above-identified patent and that said Letters Patent is hereby corrected as shown below:

Column 1, lines 31-35, "(A1-A5) are the amino acid residues in the positions A1 to A5 of the A chain of human insulin [or animal insulin]," should read --(A1-A5) are the amino acid residues in the position A1 to A5 of the A chain of human insulin or animal insulin,--.

Column 2, after line 26, please insert

--in which
      (A1-A5) are the amino acid residues in the positions A1 to A5 of the A chain of human insulin [or animal insulin],
      (A12-A19) are the amino acid residues in the positions A12 to A19 of the A chain of human insulin or animal insulin,
      A21 is Asn, Asp, Gly, Ser, Thr, or Ala,
      (B8 - B18) are the amino acid residues in the positions B8 to B18 of the B chain of human insulin or animal insulin,
      (B20-B26) are the amino acid residues in the positions B20 to B26 of the B chain of human insulin or animal insulin,
      A8, A9, A10 are the amino acid residues in the positions A8, A9, and A10 of the A chain of human insulin or animal insulin,
      B30 is -OH or the amino acid residue in portion B30 of the B chain of human insulin or animal insulin,
      B1 is a phenylalanine residue (Phe) or a hydrogen atom,
      B3 is a naturally occurring basic amino acid residue,

UNITED STATES PATENT AND TRADEMARK OFFICE
CERTIFICATE OF CORRECTION

PATENT NO.       : 6,221,633 C1
APPLICATION NO.  : 90/006928
DATED            : May 22, 2007
INVENTOR(S)      : Johann Ertl et al.

It is certified that error appears in the above-identified patent and that said Letters Patent is hereby corrected as shown below:

B27, B28 and B29 are the amino acid residues in the positions B27, B28, B29 of the B chain of human insulin or animal insulin, or in each case are another naturally occurring amino acid residue, where at least one of the amino acid residues in the positions B27, B28, and B29 of the B chain is replaced by another naturally occurring amino acid residue which is selected from the group consisting of the neutral or acidic amino acids.

This certificate supersedes Certificate of Correction issued October 23, 2007.

Signed and Sealed this

Twentieth Day of November, 2007

JON W. DUDAS
*Director of the United States Patent and Trademark Office*

UNITED STATES PATENT AND TRADEMARK OFFICE
CERTIFICATE OF CORRECTION

PATENT NO. : 6,221,633 C1  Page 1 of 1
APPLICATION NO. : 90/006928
DATED : May 22, 2007
INVENTOR(S) : Johann Ertl et al.

It is certified that error appears in the above-identified patent and that said Letters Patent is hereby corrected as shown below:

Column 1, lines 31-35, "(A1-A5) are the amino acid residues in the positions A1 to A5 of the A chain of human insulin [or animal insulin]," should read --(A1-A5) are the amino acid residues in the position A1 to A5 of the A chain of human insulin or animal insulin,--.

Column 2, after line 26, please insert

--in which
(A1-A5) are the amino acid residues in the positions A1 to A5 of the A chain of human insulin [or animal insulin],
(A12-A19) are the amino acid residues in the positions A12 to A19 of the A chain of human insulin or animal insulin,
A21 is Asn, Asp, Gly, Ser, Thr, or Ala,
(B8 - B18) are the amino acid residues in the positions B8 to B18 of the B chain of human insulin or animal insulin,
(B20-B26) are the amino acid residues in the positions B20 to B26 of the B chain of human insulin or animal insulin,
A8, A9, A10 are the amino acid residues in the positions A8, A9, and A10 of the A chain of human insulin or animal insulin,
B30 is -OH or the amino acid residue in portion B30 of the B chain of human insulin or animal insulin,
B1 is a phenylalanine residue (Phe) or a hydrogen atom,
B3 is a naturally occurring basic amino acid residue,
B27, B28 and B29 are the amino acid residues in the positions B27, B28, B29 of the B chain of human insulin or animal insulin, or in each case are another naturally occurring amino acid residue, where at least one of the amino acid residues in the positions B27, B28, and B29 of the B chain is replaced by another naturally occurring amino acid residue which is selected from the group consisting of the neutral or acidic Signed and Sealed this Eleventh Day of December, 2007

JON W. DUDAS
*Director of the United States Patent and Trademark Office*

(12) EX PARTE REEXAMINATION CERTIFICATE (5767th)
United States Patent
Ertl et al.

(10) Number: US 6,221,633 C1
(45) Certificate Issued: May 22, 2007

(54) INSULIN DERIVATIVES HAVING A RAPID ONSET OF ACTION

(75) Inventors: Johann Ertl, Bremthal (DE); Paul Habermann, Eppstein (DE); Karl Geisen, Frankfurt (DE); Gerhard Seipke, Hofheim (DE)

(73) Assignee: Aventis Pharma Deutschland GmbH, Frankfurt am Main (DE)

Reexamination Request:
No. 90/006,928, Feb. 2, 2004

Reexamination Certificate for:
Patent No.: 6,221,633
Issued: Apr. 24, 2001
Appl. No.: 09/099,307
Filed: Jun. 18, 1998

Certificate of Correction issued Mar. 5, 2002.

(30) Foreign Application Priority Data

Jun. 20, 1997 (DE) ........................................ 197 26 167

(51) Int. Cl.
*C12N 15/17* (2006.01)
*C12N 15/63* (2006.01)
*C12N 1/21* (2006.01)
*C12N 14/62* (2006.01)
*A61K 38/28* (2006.01)

(52) U.S. Cl. .................... 435/69.4; 435/243; 435/320.1; 435/325; 536/23.1; 530/303; 514/3; 514/866

(58) Field of Classification Search ....................... None
See application file for complete search history.

(56) References Cited

U.S. PATENT DOCUMENTS 5,034,415 A * 7/1991 Rubin ........................ 514/560

OTHER PUBLICATIONS

Beintema, JJ, and RN Campagne, "Molecular Evolution of Rodent Insulins", *Mol. Biol. Evol.* 4(1):10–18, 1987.

\* cited by examiner

*Primary Examiner*—Marianne P. Allen

(57) ABSTRACT

The present invention relates to insulin derivatives which in comparison to human insulin, have an accelerated onset of action, to a process for their preparation and to their use, in particular in pharmaceutical preparations for the treatment of diabetes mellitus. In particular, the present invention relates to insulin derivatives or physiologically tolerable salts thereof in which asparagine (Asn) in position B3 of the B chain is replaced by a naturally occurring basic amino acid residue and at least one amino acid residue in the positions B27, B28 or B29 of the B chain is replaced by another naturally occurring amino acid residue, it optionally being possible for asparagine (Asn) in position 21 of the A chain to be replaced by Asp, Gly, Ser, Thr or Ala and for phenylalanine (Phe) in position B1 of the B chain and the amino acid residue in position B30 of the B chain to be absent.

EX PARTE REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

ONLY THOSE PARAGRAPHS OF THE SPECIFICATION AFFECTED BY AMENDMENT ARE PRINTED HEREIN.

Column 3, lines 6–15:

Preferably, the insulin derivative or its physiologically tolerable salt is of formula I

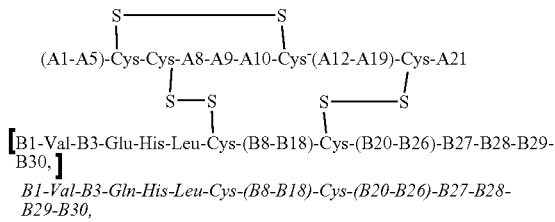

[B1-Val-B3-Glu-His-Leu-Cys-(B8-B18)-Cys-(B20-B26)-B27-B28-B29-B30,]

*B1-Val-B3-Gln-His-Leu-Cys-(B8-B18)-Cys-(B20-B26)-B27-B28-B29-B30,* in which
 (A1-A5) are the amino acid residues in the positions A1 to A5 of the A chain of human insulin [or animal insulin],
 (A12-A19) are the amino acid residues in the positions A12 to A19 of the A chain of human insulin or animal insulin,
 A21 is Asn, Asp, Gly, Ser, Thr, or Ala,
 (B8-B18) are the amino acid residues in the positions B8 to B18 of the B chain of human insulin or animal insulin,
 (B20-B26) are the amino acid residues in the positions B20 to B26 of the B chain of human insulin or animal insulin,
 A8,A9, A10 are the amino acid residues in the positions A8, A9, and A10 of the A chain of human insulin or animal insulin,
 B30 is —OH or the amino acid residue in poriton B30 of the B chain of human insulin or animal insulin,
 B1 is a phenylalanine residue (Phe) or a hydrogen atom,
 B3 is a naturally occurring basic amino acid residue,
 B27, B28, and B29 are the amino acid residues in the positions B27, B28, B29 of the B chain of human insulin or animal insulin, or in each case are another naturally occurring amino acid residue, where at least one of the amino acid residues in the positions B27, B28, and B29 of the B chain is replaced by another naturally occurring amino acid residue which is selected from the group consisting of the neutral or acidic amino acids.

AS A RESULT OF REEXAMINATION, IT HAS BEEN DETERMINED THAT:

Claims 1, 2, 33, 56, 59, 61 and 63 are determined to be patentable as amended.

Claims 3–32, 34–55, 57–58, 60, 62 and 64, dependent on an amended claim, are determined to be patentable.

New claims 65 and 66 are added and determined to be patentable.

1. An insulin derivative or a physiologically tolerable salt thereof, in which asparagine (Asn) in position B3 of the B chain is replaced by a naturally occurring basic amino acid residue and at least one amino acid residue in the positions B27, B28, or B29 of the B chain is replaced by another naturally occurring neutral or acidic amino acid residue, *and wherein (A1–A5) are the amino acid residues in the positions A1 to A5 of the A chain of human insulin.*

2. An insulin derivative or a physiologically tolerable salt thereof [as claimed in claim 1,] of formula I

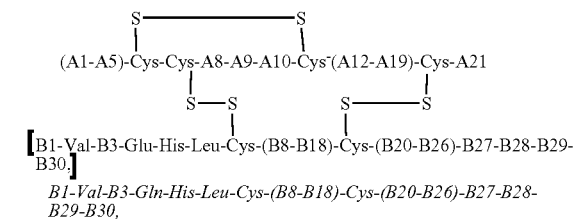

[B1-Val-B3-Glu-His-Leu-Cys-(B8-B18)-Cys-(B20-B26)-B27-B28-B29-B30.]

*B1-Val-B3-Gln-His-Leu-Cys-(B8-B18)-Cys-(B20-B26)-B27-B28-B29-B30,*

33. An insulin derivative or a physiologically tolerable salt thereof as claimed in claim 1, wherein the amino acid residue in position A21 of the A chain is an asparagine residue ([Asp] *Asn*).

56. The isolated or purified nucleic acid of claim 55, [having the sequence of SEQ ID NO.11.] *which codes for a precursor of an insulin derivative having the sequence of SEQ ID NO.: 11.*

59. The isolated or purified nucleic acid of claim 55, [having the sequence of SEQ ID NO.:6.] *which codes for a precursor of an insulin derivative having the sequence of SEQ ID NO.: 6.*

61. The isolated or purified nucleic acid of claim 55, [having the sequence of SEQ ID NO.:8.] *which codes for a precursor of an insulin derivative having the sequence of SEQ ID NO.: 8.*

63. The isolated or purified nucleic acid of claim 55, [having the sequence of SEQ ID NO.:7.] *which codes for a precursor of an insulin derivative having the sequence of SEQ ID NO.: 7.*

*65. An insulin derivative or a physiologically tolerable salt thereof, said derivative or salt comprising a naturally occurring basic amino acid residue at position B3 of the B chain and a naturally occurring neutral or acidic amino acid residue at one or more of positions B27, B28, and B29 of the B chain, wherein positions A1–A5 of the A chain of the derivative are the human insulin residues.*

*66. A genetically engineered insulin derivative of a wild-type insulin, or a physiologically tolerable salt thereof, said derivative comprising (1) a naturally-occurring basic amino acid residue at position B3 of the B chain whereas the wild-type insulin has an asparagine (ASN) in position B3 of the B chain, (2) a naturally occurring neutral or acidic* amino acid residue at one or more positions B27, B28, and B29 of the B chain, wherein the naturally-occurring neutral or acidic amino acid residue differs from the residue present at position B27, B28, and/or B29 in the wild-type insulin, and (3) positions A1–A5 of the A chain of the derivative are the human insulin residues.

* * * * *